(12) United States Patent
Pacetti et al.

(10) Patent No.: US 8,673,334 B2
(45) Date of Patent: Mar. 18, 2014

(54) STENT COATINGS COMPRISING HYDROPHILIC ADDITIVES

(75) Inventors: Stephen D. Pacetti, San Jose, CA (US); Yiwen Tang, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 424 days.

(21) Appl. No.: 11/903,176

(22) Filed: Sep. 19, 2007

(65) Prior Publication Data

US 2008/0118543 A1 May 22, 2008

Related U.S. Application Data

(62) Division of application No. 10/431,711, filed on May 8, 2003, now Pat. No. 7,279,174.

(51) Int. Cl.
*A61K 47/00* (2006.01)
*A61F 2/00* (2006.01)

(52) U.S. Cl.
USPC ............................................................ 424/423

(58) Field of Classification Search
None
See application file for complete search history.

(56) References Cited

U.S. PATENT DOCUMENTS

| | | | |
|---|---|---|---|
| 590,263 A | 9/1897 | Henry | |
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | |
| 4,752,624 A | 6/1988 | Kim et al. | |
| 4,800,882 A | 1/1989 | Gianturco | |
| 4,882,168 A | 11/1989 | Casey et al. | |
| 4,883,699 A | 11/1989 | Aniuk et al. | |
| 4,886,062 A | 12/1989 | Wiktor | |
| 4,931,287 A * | 6/1990 | Bae et al. ...................... | 424/484 |
| 4,941,870 A | 7/1990 | Okada et al. | |
| 4,977,901 A | 12/1990 | Ofstead | |
| 5,019,096 A | 5/1991 | Fox, Jr. et al. | |
| 5,079,272 A | 1/1992 | Allegrezza et al. | |
| 5,100,992 A | 3/1992 | Cohn et al. | |
| 5,112,457 A | 5/1992 | Marchant | |
| 5,133,742 A | 7/1992 | Pinchuk | |
| 5,163,952 A | 11/1992 | Froix | |
| 5,165,919 A | 11/1992 | Sasaki et al. | |
| 5,219,980 A | 6/1993 | Swidler | |
| 5,258,020 A | 11/1993 | Froix | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,306,786 A | 4/1994 | Moens et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,426,158 A | 6/1995 | Mueller et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,485,496 A | 1/1996 | Lee et al. | |
| 5,516,881 A | 5/1996 | Lee et al. | |
| 5,569,463 A | 10/1996 | Helmus et al. | |
| 5,578,073 A | 11/1996 | Haimovich et al. | |
| 5,584,877 A | 12/1996 | Myiake et al. | |
| 5,605,696 A * | 2/1997 | Eury et al. .................... | 424/423 |
| 5,607,467 A | 3/1997 | Froix | |
| 5,609,629 A | 3/1997 | Fearnot et al. | |
| 5,610,241 A | 3/1997 | Lee et al. | |
| 5,616,338 A | 4/1997 | Fox, Jr. et al. | |
| 5,624,411 A | 4/1997 | Tuch | |
| 5,628,730 A | 5/1997 | Shapland et al. | |
| 5,644,020 A | 7/1997 | Timmermann et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,674,242 A | 10/1997 | Phan et al. | |
| 5,679,400 A | 10/1997 | Tuch | |
| 5,700,286 A | 12/1997 | Tartaglia et al. | |

(Continued)

FOREIGN PATENT DOCUMENTS

| DE | 42 24 401 | 1/1994 |
|---|---|---|
| EP | 0 301 856 | 2/1989 |

(Continued)

OTHER PUBLICATIONS

Kamath et. al, Advanced Drug Delivery Reviews, 58 (2006) 4112-436.*
Tesfamariam, Journal fo Cardiovascular Pharmacology, 51 (2008) 118-125.*
Polyethylene Amine (en.wikipedia.org/wiki/Polyethylene_amine) (downloaded Dec. 16, 2011).*
Polyethylenimine (en.wikipedia.org/wiki/Polyethylenimine) (downloaded Dec. 16, 2011).*
Online Conversion (www.onlineconversion.com/energy.htm) (downloaded Dec. 16, 2011).*
"Additive" Definition at http://www.thefreedictionary.com/ additive) (retireved from the internet May 4, 2013).*
U.S. Appl. No. 09/894,293, filed Jun. 27, 2001, Roorda et al.
U.S. Appl. No. 10/198,912, filed Jul. 19, 2002, Ding et al.
U.S. Appl. No. 10/177,154, filed Jun. 21, 2002, Hossainy et al.
U.S. Appl. No. 10/251,111, filed Sep. 19, 2002, Hossainy et al.
U.S. Appl. No. 10/376,348, filed Feb. 26, 2003, Ding et al.
U.S. Appl. No. 10/428,691, filed May 1, 2003, Pacetti.
International Search Report mailed May 10, 2004, for PCT application No. PCT/US2004/009011, filed Mar. 23, 2004, 8 pgs.

(Continued)

*Primary Examiner* — Dennis Heyer
(74) *Attorney, Agent, or Firm* — Squire Sanders (US) LLP (57) ABSTRACT

A coating for implantable medical devices and a method for fabricating thereof are disclosed. The coating includes a mixture of a hydrophobic polymer and a polymeric hydrophilic additive, wherein the hydrophobic polymer and the hydrophilic additive form a physically entangled or interpenetrating system.

23 Claims, 1 Drawing Sheet

(56) References Cited

U.S. PATENT DOCUMENTS

| | | |
|---|---|---|
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,631 A | 5/1999 | Wang et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,962,620 A | 10/1999 | Reich et al. |
| 5,964,744 A | 10/1999 | Balbierz et al. |
| 5,971,954 A | 10/1999 | Conway et al. |
| 5,980,928 A | 11/1999 | Terry |
| 5,980,972 A | 11/1999 | Ding |
| 5,993,972 A | 11/1999 | Reich et al. |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,030,634 A | 2/2000 | Wu et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A * | 8/2000 | Whitbourne et al. ......... 424/423 |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,156,344 A | 12/2000 | Kim et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,224,893 B1 | 5/2001 | Langer et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,331,578 B1 * | 12/2001 | Turner et al. .................. 523/105 |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,384,046 B1 * | 5/2002 | Schuler et al. ................ 514/291 |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |

(56) References Cited

U.S. PATENT DOCUMENTS

| | | |
|---|---|---|
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,861,503 B2 * | 3/2005 | Shalaby .................. 528/425 |
| 7,005,137 B1 | 2/2006 | Hossainy et al. |
| 7,008,635 B1 | 3/2006 | Coury et al. |
| 7,094,256 B1 | 8/2006 | Shah et al. |
| 7,217,426 B1 | 5/2007 | Hossainy |
| 7,247,313 B2 | 7/2007 | Roorda et al. |
| 2001/0007083 A1 | 7/2001 | Roorda |
| 2001/0014717 A1 * | 8/2001 | Hossainy et al. .............. 525/60 |
| 2001/0018469 A1 | 8/2001 | Chen et al. |
| 2001/0020011 A1 | 9/2001 | Mathiowitz et al. |
| 2001/0027340 A1 * | 10/2001 | Wright et al. ............... 623/1.15 |
| 2001/0029351 A1 | 10/2001 | Falotico et al. |
| 2001/0273640 | 10/2001 | Wright et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0065551 A1 | 5/2002 | Koole et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 * | 7/2002 | Llanos et al. ................. 428/421 |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0133183 A1 | 9/2002 | Lentz et al. |
| 2002/0142039 A1 | 10/2002 | Claude |
| 2002/0150549 A1 | 10/2002 | Vogt et al. |
| 2002/0155212 A1 | 10/2002 | Hossainy |
| 2002/0165608 A1 | 11/2002 | Llanos et al. |
| 2002/0176849 A1 | 11/2002 | Slepian |
| 2001/0188037 | 12/2002 | Chudzik et al. |
| 2002/0183581 A1 | 12/2002 | Yoe et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0065382 A1 | 4/2003 | Fischell et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0144727 A1 * | 7/2003 | Rosenthal et al. ........... 623/1.15 |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047911 A1 * | 3/2004 | Lyu et al. ...................... 424/487 |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0127978 A1 * | 7/2004 | Sparer et al. ................. 623/1.46 |
| 2005/0191332 A1 * | 9/2005 | Hossainy ..................... 424/423 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| JP | 2002-506369 | 2/2002 |
| JP | 2002-315823 | 10/2002 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/58690 | 12/1998 |
| WO | WO 99/01118 | 1/1999 |
| WO | WO 99/38546 | 8/1999 |
| WO | WO 99/63981 | 12/1999 |
| WO | WO 00/02599 | 1/2000 |

(56) References Cited

FOREIGN PATENT DOCUMENTS

| WO | WO 00/12147 | 3/2000 |
|----|----|----|
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/010975 | 2/2004 |

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Amendment and Response to OA of a related U.S. Appl. No. 11/903,011, mailed Mar. 18, 2009, 13 pgs.

IUPAC Compendium of Chemical Terminology $2^{nd}$ Ed. (1997), 1 pg.

Kamath et al., "The Taxus™ drug-eluting stent: A new paradigm in controlled delivery", Advanced Drug Delivery Reviews 58, pp. 412-436 (2006).

Tesfamariam, "Drug Release Kinetics from Stent Device-Based Delivery Systems", Journal of Cardiovascular Pharmacology 51, pp. 118-125 (2008).

Notification of Refusal, issued by JPO on Aug. 17, 2010, in connection with Appl. No. 2006-532338, 3 pgs.

Translation of a Notification of Refusal, issued by JPO on Aug. 17, 2010, in connection with Appl. No. 2006-532338, 3 pgs.

* cited by examiner

STENT COATINGS COMPRISING HYDROPHILIC ADDITIVES

RELATED APPLICATIONS

This application is a divisional of U.S. application Ser. No. 10/431,711 filed 8 May 2003, now U.S. Pat. No. 7,279,174 which is incorporated by reference as if fully set forth, including any figures, herein.

FIELD

This invention relates to implantable medical devices such as stents. More particularly, the invention relates to materials that can be used to coat stents.

BACKGROUND

In the field of medical technology, there is frequently a necessity to administer drugs locally. To provide an efficacious concentration to the treatment site, systemic administration of medication often produces adverse or toxic side effects for the patient. Local delivery is a preferred method of treatment in that smaller total levels of medication are administered in comparison to systemic dosages, but are concentrated at a specific site. For the treatment of vascular lesions, stents can be modified with a polymeric coating to provide local drug delivery capabilities.

Examples of polymers that can be used to coat stents or other implantable devices include hydrophobic polymers, for example, poly(meth)acrylates, such as poly(n-butyl methacrylate) (PBMA) and copolymers or terpolymers having units derived from n-butyl methacrylate (BMA). PBMA and BMA-based coatings can provide effective control of the rate of release of a drug from a stent. In addition, PBMA and BMA-based polymers are biocompatible, have good adhesion to the underlying stent surface, are easily processable, and possess good physical and mechanical properties such as ability to withstand elongation, compression, and shear that the stent undergoes during crimping onto the catheter, delivery to the lesion site, and expansion.

The properties of PBMA and BMA-based stent coatings can be improved, however. For example, permeability of such coatings can be too low, particularly for drugs having higher molecular weights, leading to potentially insufficient supply of the drug to the diseased site. An ability to better regulate the rate of release through the coatings is desired. The present invention provides such coatings.

SUMMARY

An implantable medical device comprising a coating is provided, the coating includes a mixture of at least one poly(meth)acrylate and at least one polyalkylene glycol, wherein the macromolecular chains of the poly(meth)acrylate and the polyalkylene glycol form a physically entangled or interpenetrating system. Examples of the poly(meth)acrylate include poly(methyl methacrylate), poly(ethyl methacrylate), poly(n-propyl methacrylate), poly(iso-propyl methacrylate), poly(n-butyl methacrylate), poly(iso-butyl methacrylate), poly(tert-butyl methacrylate), poly(methyl acrylate), poly(ethyl acrylate), poly(n-propyl acrylate), poly(iso-propyl acrylate), poly(n-butyl acrylate), poly(iso-butyl acrylate), and mixtures thereof. Examples of the polyalkylene glycol include poly(ethylene glycol), poly(ethylene oxide), poly(propylene glycol), poly(ethylene oxide-co-propylene oxide), poly(trimethylene glycol), poly(tetramethylene glycol), and mixtures thereof.

An implantable medical device comprising a coating is provided, the coating includes a mixture of at least one hydrophobic polymer and at least one polymeric hydrophilic compound, wherein the macromolecular chains of the hydrophobic polymer and the hydrophilic compound form a physically entangled or interpenetrating system. The hydrophobic polymer can include poly(meth)acrylates, vinyl polymers, polyolefins, halogenanated polymers, polymers having urethane groups, polybutyrals, nylon, silicones, polycarbonate, or polysulfone. The polymeric hydrophilic compound can include polyalkylene glycols, hyaluronic acid, chondroitan sulfate, chitosan, glucosaminoglucans, dextran, dextrin, dextran sulfate, cellulose acetate, carboxymethyl cellulose, hydroxyethyl cellulose, cellulosics, polypeptides, poly(2-hydroxyethyl methacrylate), polyacrylamide, polyacrylimide, poly(ethylene amine), poly(allyl amine), poly(vinyl pyrrolidone), poly(vinyl alcohol), poly(acrylic acid), poly(methacrylic acid), acrylic acid copolymers, methacrylic acid copolymers, polyvinyl alkyl ethers, non-ionic tetrafunctional block-copolymer surfactants, gelatin, collagen, albumin, chitin, heparin, elastin, fibrin, and mixtures thereof.

A medical article comprising an implantable substrate and a coating is provided, the coating includes a bulk polymer, an additive polymer in less quantity in the coating that the bulk polymer, the additive polymer being entangled or interpenetrated with the bulk polymer, and a drug.

A method for fabricating a coating for an implantable medical device is provided, the method comprises forming a coating on the device, the coating including a mixture of at least one hydrophobic polymer and at least one polymeric hydrophilic compound, wherein the macromolecular chains of the hydrophobic polymer and the hydrophilic compound form a physically entangled or intertwined system.

DETAILED DESCRIPTION

A coating for an implantable medical device, such as a stent, can include an optional primer layer, a drug-polymer layer, and an optional topcoat layer. The drug-polymer layer can be applied directly onto at least a part of the stent surface to serve as a reservoir for an active agent or a drug which is incorporated into the drug-polymer layer. An optional primer layer can be applied between the stent and the drug-polymer layer to improve the adhesion of the drug-polymer layer to the stent. An optional topcoat layer can be applied over at least a part of the drug-polymer layer to reduce the rate of release of the drug from the reservoir.

The topcoat layer, if used, is the outermost layer of the stent coating. If the topcoat layer is not used, the drug-polymer layer is the outermost layer of the stent coating. The drug-polymer and/or topcoat layer of the stent coating can include at least one hydrophobic polymer. To regulate a rate of release of the drug from the drug-polymer layer the hydrophobic polymer(s) can be physically mixed or blended with at least one polymeric hydrophilic additive to form a polymer system where the macromolecular chains of the hydrophobic polymer and the hydrophobic additive are physically entangled, miscible, and/or interpenetrating. This polymer system can be, in one embodiment, the outermost region or layer of the coating.

Hereinafter, the hydrophobic polymer is also referred to as "polymer," and polymeric hydrophilic additive is also referred to as "additive." The term "physically entangled" is defined hereinafter as a polymer/additive composition in which neither the polymer nor the additive forms a separate phase domain having a size larger than about 100 nanometers, such as the size larger than about 200 nanometers, for example, larger than about 300 nanometers. The size of the domain is determined by the largest linear dimension of the domain particle, e.g., by the diameter of a particle in case the domain particles are spheres. The definition of "physically entangled" also includes a condition that once the polymer and the additive have become physically entangled, they do not disentangle but remain physically entangled for the duration of the service of the coating or until the drug has been released from the coating.

The hydrophobic polymer and the hydrophobic additive are defined hereinafter as "miscible" if the thermogram of the polymer/additive mixture shows substantially no thermal transitions attributable to either the essentially pure polymer or the essentially pure additive. The thermogram can be obtained by a standard method of thermal analysis known to those having ordinary skill in the art, for example, by the method of differential scanning calorimetry.

The term "interpenetrating" is defined as the polymer/additive system where the polymer and the additive form an interpenetrating polymer network (IPN). The definition of the IPN used by the International Union of Pure and Applied Chemistry (IUPAC) is adopted herein. The IUPAC describes the IPN as a polymer comprising two or more networks which are at least partially interlaced on a molecular scale, to form both chemical and physical bonds between the networks. The networks of an IPN cannot be separated unless chemical bonds are broken. In other words, an IPN structure represents two or more polymer networks that are partially chemically cross-linked and partially physically entangled.

To define the terms "hydrophobic" and "hydrophilic" for the purposes of the present invention, one of the two criteria can be used. According to one criterion, a component in the polymer/additive system (i.e., the polymer or the additive) can be classified by the value of the component's equilibrium water adsorption. Whichever component in the polymer/additive system has the greater value of the equilibrium water adsorption at room temperature is considered hydrophilic and the other component is considered hydrophobic. If more than two components are used in the polymer/additive system, then each can be ranked in order of its equilibrium water adsorption value. In one embodiment, the polymer is considered hydrophobic if it has an equilibrium water adsorption less than 10 mass % at room temperature, and the additive is considered hydrophilic if it has an equilibrium water adsorption at room temperature of 10 mass % or greater.

According to another criterion, a component in the polymer/additive system can be classified by the value of the component's Hildebrand solubility parameter δ. The term "Hildebrand solubility parameter" refers to a parameter measuring the cohesion of a substance and is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

Whichever component in the polymer/additive system has lower δ value compared to the δ value of the other component in the blend is designated as a hydrophobic component, and the other component with higher δ value is designated as hydrophilic. If more than two components are used in the blend, then each can be ranked in order of its δ value. In one exemplary embodiment, the δ value defining the boundary between the hydrophobic and hydrophilic components of the polymer/additive system can be about 10.7 $(cal/cm^3)^{1/2}$.

Hydrophobic substances typically have a low δ value. In one embodiment, a component in the polymer/additive system that is "hydrophobic" can have a Hildebrand solubility parameter lower than about 10.7 $(cal/cm^3)^{1/2}$. A component in the polymer/additive system that is "hydrophilic" can have a solubility parameter greater than about 10.7 $(cal/cm^3)^{1/2}$.

To make the polymer/additive mixture, the polymer can be blended with the additive and the blend can be dissolved in a solvent or in a system comprising a mixture of solvents. The term "dissolved" means that the polymer/additive blend, when combined with a suitable solvent or a mixture of solvents, is capable of forming a system which can be applied on a stent by a common technique, such as spraying or dipping. The solvent or a mixture of solvents can be selected by those having ordinary skill in the art depending, among other factors, on the nature of the polymer and the additive.

The polymer/additive solution can be then applied on the stent by a commonly known technique known to those having ordinary skill in the art, for example, by spraying or dipping, followed by drying, for example, by baking. The polymer/additive solution can be used to form the topcoat layer and/or the drug-polymer layer of the stent coating.

The combined mass concentration of the polymer and the additive in the polymer/additive solution can be between about 1% and about 10%, for example, about 2%. A ratio between the hydrophobic polymer and the polymeric hydrophilic additive in the polymer/additive solution can be between about 99:1 and about 9:1, such as between about 74:1 and about 14:1, more narrowly between about 49:1 and about 19:1. For example, for a polymer/additive solution containing about 2 mass % of the hydrophobic polymer, the concentration of the polymeric hydrophilic additive can be between about 0.04 and about 0.1 mass % of the total mass of the solution.

The polymer/additive solution can be prepared by various alternative methods. For example, the hydrophobic polymer and the polymeric hydrophilic additive can be dissolved separately to obtain a hydrophobic polymer solution and a polymeric hydrophilic additive solution, followed by combining the two solutions to form the polymer/additive solution. Alternatively, the hydrophobio polymer can be dissolved first to form the hydrophobic polymer solution, followed by adding the polymeric hydrophilic additive to the hydrophobic polymer solution to form the polymer/additive solution. As another alternative, the additive can be dissolved first to form the additive solution followed by adding the polymer to form the polymer/additive solution.

Examples of hydrophobic polymers include poly(meth)acrylates. The term "poly(meth)acrylates" refers to both polymethacrylates and polyacrylates. Examples of poly(meth)acrylates that can be used include homo- and copolymers of butyl methacrylate, for example PBMA, poly(vinylidene fluoride-co butyl methacrylate), or poly(methyl methacrylate-co-butyl methacrylate). Representative examples of other hydrophobic polymers that can be used in practice of the present invention include the following polymers and mixtures thereof:

(a) poly(meth)acrylates other than PBMA or BMA-based polymethacrylates, such as poly(methyl methacrylate), poly(ethyl methacrylate), poly(n-propyl methacrylate), poly(iso-propyl methacrylate), poly(iso-butyl methacrylate), poly(tert-butyl methacrylate), poly(methyl acrylate), poly(ethyl acrylate), poly(n-propyl acrylate), poly(iso-propyl acrylate), poly(n-butyl acrylate), and poly(iso-butyl acrylate);

(b) vinyl polymers such as poly(ethylene-co-vinyl alcohol), for example, poly(ethylene-co-vinyl alcohol) having a molar content of ethylene-derived units of at least 44%, poly(ethylene-co-vinyl acetate), poly(vinyl acetate), polystyrene, poly(styrene-co-iso-butylene), poly(styrene-co-ethylene-co-butylene-co-styrene) terpolymers, and poly(styrene-co-butadiene-co-styrene) terpolymers;

(c) polyolefins, for example, atactic polypropylene;

(d) halogenated (e.g., fluorinated or chlorinated) polymers such as poly(vinyl fluoride), poly(vinylidene fluoride), polyhexafluoropropene, poly(hexafluoropropene-co-vinylidene fluoride), poly(ethylene-co-hexafluoropropene), various grades of amorphous TEFLON (including polytetrafluoroethylene) available from E.I. Du Pont de Nemours & Co., poly(vinyl chloride), and poly(vinylidene chloride);

(e) polymers having urethane groups, such as polyether urethanes, polyester urethanes, polyurethaneureas, polycarbonate urethanes, and silicone urethanes; and (f) polybutyrals, nylon, silicones, polycarbonate, and polysulfone.

Representative examples of polymeric hydrophilic additives that can be used in practice of the present invention include hyaluronic acid, chondroitan sulfate, chitosan, glucosaminoglucans, dextran, dextrin, dextran sulfate, cellulose acetate, carboxymethyl cellulose, hydroxyethyl cellulose, cellulosics, poly(ethylene glycol)(PEG), poly(ethylene oxide), poly(propylene glycol), PLURONIC, TETRONIC, poly(trimethylene glycol), poly(tetramethylene glycol), polypeptides, poly(2-hydroxyethyl methacrylate), polyacrylamide, polyacrylimide, poly(ethylene amine), poly(allyl amine), poly(vinyl pyrrolidone), poly(vinyl alcohol), poly (acrylic acid), poly(methacrylic acid), acrylic acid copolymers, methacrylic acid copolymers, polyvinyl alkyl ethers such as poly(vinylmethyl ether) or poly(vinylethyl ether); gelatin, collagen, albumin, chitin, heparin, elastin, fibrin and mixtures thereof. PLURONIC is a trade name of a poly(ethylene oxide-co-propylene oxide). TETRONIC is a trade name of a family of non-ionic tetrafunctional block-copolymer surfactants. PLURONIC and TETRONIC are available from BASF Corp. of Parsippany, N.J.

To achieve the physical entanglement of the hydrophobic polymer and polymeric hydrophilic additive, at least one polymer and at least one additive can be blended together in a common solvent system that includes at least one very volatile solvent, followed by applying the solution onto a stent, for example, by spraying. As used herein, "very volatile solvent" means a solvent that has a vapor pressure greater than 30 Torr at ambient temperature. Examples of very volatile solvent include acetone and methyl ethyl ketone. Alternatively, to physically entangle the hydrophobic polymer and polymeric hydrophilic additive, the polymer and the additive can be blended in the melt, and then applied to the stent from the melt, for example by curtain coating.

One way of forming an interpenetrating system of the hydrophobic polymer and polymeric hydrophilic additive is by blending the polymer and the additive in a solvent, or solvent blend, in which both components are soluble. The solution can be applied onto a stent, for example, by spraying, followed by the removal of the solvent by drying. For the polymer and the additive which are capable of forming an interpenetrating system, the polymers and the additive are expected to interpenetrate while still in solution, and to remain interpenetrated upon solvent removal.

Alternatively, to form an interpenetrating system of the hydrophobic polymer and polymeric hydrophilic additive, the polymer and additive, which can be polymerized according to two different mechanisms, can be selected. For example, the hydrophobic component can be a carbonate urethane that is polymerized by condensation reactions between isocyanate and hydroxyl groups, while the hydrophilic additive can be poly(2-hydroxyethyl methacrylate) that polymerizes by a free radical mechanism. The monomers may be dissolved in a common solvent system, applied to the stent, and then polymerized directly on the stent.

As another alternative way of forming an interpenetrating system of the hydrophobic polymer and polymeric hydrophilic additive, a high molecular weight polymer and additive can be selected, each component having reactive or associative groups that can interact with the reactive or associative groups of the other component. For example, such hydrophilic additive as hydroxy terminated PEG can be blended with a high molecular weight, hydrophobic polyurethane with active isocyanate groups along the backbone. The additive and the polymer can be blended in solution, sprayed onto a stent, followed by curing. Although sometimes the two components may be not miscible, the covalent bonds between them can still prevent phase separation.

To facilitate the formation of an entangled and/or interpenetrating hydrophobic polymer-polymeric hydrophilic additive system, the polymer and the additive can be selected in such a way that the chain lengths of the polymer and the additive, as determined by degree of polymerization, are such as to promote the entanglement and/or interpenetration of the macromolecules of the polymer and the additive. The term "degree of polymerization" refers to a number of repeating monomeric units in a single macromolecule. The chain lengths that promote the formation of an entangled and/or interpenetrating network can be such that the contour length of the hydrophilic additive lies in the range of between about 10% and about 100% of the contour length of the hydrophobic polymer, for example, between 50% and 100%, such as 80%. The term "contour length" refers to the combined length of all bonds along the main chain (the backbone) of a macromolecule. The contour length can be approximated as the degree of polymerization multiplied by the number of bonds in the repeat unit. An average bond length of about 1.4 Å can be used for the computation. The following example can be used to illustrate how the molecular weights of the polymer and the additive can be chosen to achieve a proper ratio between the contour lengths of the polymer and the additive.

PBMA with a number-averaged molecular weight ($M_n$) of about 200,000, has a degree of polymerization of 1,408 and has 2 bonds in the polymer backbone per repeat unit. Thus, a contour length of a PBMA macromolecule is about 3,940 Å. Suitable hydrophilic additive to achieve entanglement can be PEG having contour lengths between about 394 Å and about 3,940 Å. PEG has 3 bonds per repeat unit, so for PEG having contour lengths between about 394 Å and about 3,940 Å, corresponding degree of polymerization is approximately between 131 and 1,313, and the corresponding $M_n$ is between about 5,780 and about 57,800.

Generally, $M_n$ of the hydrophobic polymer can be between about 50,000 and 1000,000 Daltons, for example, about 100,000 Daltons. The molecular weight of the hydrophilic additive can be between about 5,000 and about 100,000 Daltons, for example, about 40,000 Daltons. If PBMA is used as the hydrophobic polymer, the molecular weight of PBMA can be between about 100,000 and about 300,000 Daltons, for example, about 200,000 Daltons. If PEG is used as the hydrophilic additive being mixed with PBMA, the molecular weight of PEG can be between about 10,000 and about 60,000 Daltons, for example, about 20,000 Daltons.

The embodiments of the present invention are described in connection with a stent, e.g., balloon expandable or self-expandable stents; however, other implantable medical devices can also be coated. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself can be made in whole or in part from the disclosed polymeric blends.

For the drug-polymer layer, the coating can include an active agent or a drug. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutanycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and donors of nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The molecular weight of the drug can influence the choice of the molecular weights of the polymer and the additive, as well as the ratios between the polymer and the additive, since the release rate of the drugs having higher molecular weights is expected to be slower compared with the release rate of the drugs with lower molecular weights. To illustrate, when the PBMA/PEG topcoat system is used in conjunction with EVEROLIMUS (having molecular weight 958 Daltons), $M_n$ of PBMA can be between about 90,000 Daltons and about 300,000 Daltons, for example, about 190,000 Daltons and $M_n$ of PEG can be between about 6,000 Daltons and about 20,000 Daltons, for example, about 18,000 Daltons, and the mass ratio between PBMA and PEG can be between about 49:1 and about 9:1, for example, about 20:1. At the same time, in the case of estradiol (having molecular weight of 272), $M_n$ of PBMA can be between about 150,000 Daltons and about 900,000 Daltons, for example, about 300,000 Daltons and $M_n$ of PEG can be between about 10,000 Daltons and about 50,000 Daltons, for example, about 30,000 Daltons, and the mass ratio between PBMA and PEG can be between about 99:1 and about 25:1, for example about 49:1.

Embodiments of the present invention are further illustrated by the following examples.

EXAMPLE 1

A first polymer solution was prepared, the solution containing:
 (a) about 5 mass % of poly(n-butyl methacrylate) (PBMA) having $M_n$ of about 154,000; and
 (b) the balance, solvent mixture of acetone and cyclohexanone, the mixture having a mass ratio between acetone and cyclohexanone of about 4:1.

A second polymer solution was prepared, the solution containing:
 (a) about 5 mass % of poly(ethylene glycol) (PEG) having $M_n$ of about 18,000; and
 (b) the balance, solvent mixture of acetone and cyclohexanone, the mixture having a mass ratio between acetone and cyclohexanone of about 4:1.

The first polymer solution was combined with the second polymer solution to prepare a PBMA/PEG solution. The amount of the first and second polymer solutions were selected to obtain the PBMA/PEG solution having a mass ratio between PBMA and PEG of about 49:1.

Figure 1:
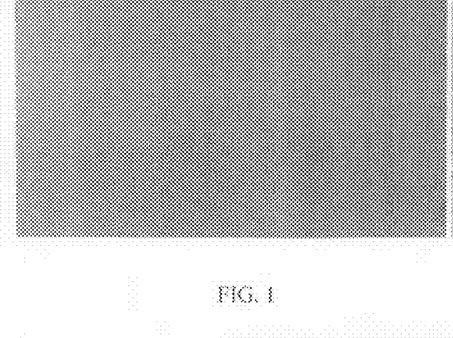
FIGS. 1-3 are optical micrographs of coatings according to various embodiments of the present invention.

The PBMA/PEG solution was cast on a glass slide, and the solvent was removed by drying at room temperature followed by baking at about 80° C. for about 1 hour. As a result, an adhered polymer film was formed on the glass slide. An optical micrograph of the dry PBMA/PEG film was taken in transmitted polarized light, as shown by FIG. 1. Under such light, amorphous polymers appear dark and crystalline polymers appear bright. As seen from FIG. 1, the PBMA/PEG system appears uniformly dark showing good miscibility of PBMA and PEG. FIG. 1 does not show that PEG forms a separate phase.

EXAMPLE 2

Figure 2:
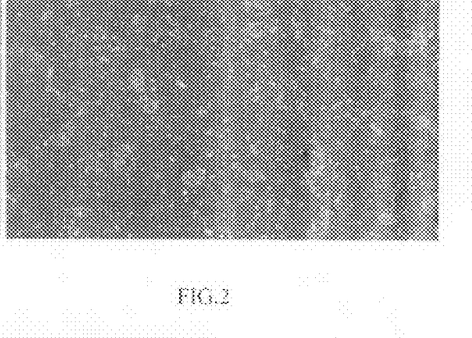

A PBMA/PEG solution was prepared as described in Example 1, except the mass ratio between PBMA and PEG in the PBMA/PEG solution was about 19:1. A polymer film was formed on a glass slide out of the PBMA/PEG solution as described in Example 1. An optical micrograph of the dry PBMA/PEG film was taken as described in Example 1. The micrograph is shown by FIG. 2. As seen from FIG. 2, the PBMA/PEG system appears mostly uniform, with some amount of the crystalline phase formed by PEG represented by bright spots on the micrograph.

EXAMPLE 3

Figure 3:
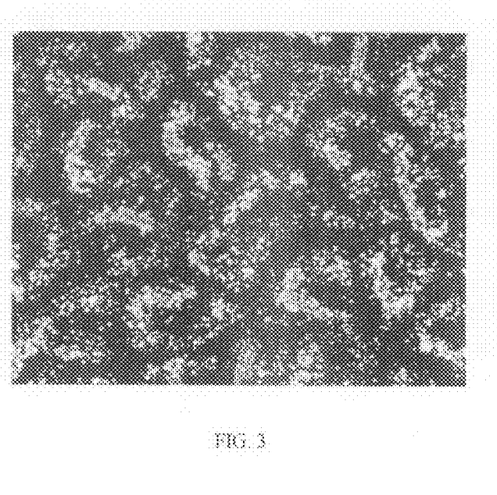

A PBMA/PEG solution was prepared as described in Example 1, except the mass ratio between PBMA and PEG in the PBMA/PEG solution was about 10:1. A polymer film was formed on a glass slide out of the PBMA/PEG solution as described in Example 1. An optical micrograph of the dry PBMA/PEG film was taken as described in Example 1. The micrograph is shown by FIG. 3. As seen from FIG. 3, the PBMA/PEG system includes visible crystalline areas. Compared with the film described in Example 2, the film shown by FIG. 3 included more substantial amount of the crystalline phase formed by PEG.

EXAMPLE 4

A first composition was prepared by mixing the following components:
  (a) between about 1.0 mass % and about 15 mass %, for example, about 2.0 mass % of poly(ethylene-co-vinyl alcohol) (EVAL); and
  (b) the balance, DMAC solvent.

The first composition was applied onto the surface of a bare 18 mm VISION stent (available from Guidant Corp.) by spraying and dried to form a primer layer. A spray coater was used, having a 0.014 fan nozzle maintained at about 60° C. with a feed pressure of about 0.2 atm (about 3 psi) and an atomization pressure of about 1.3 atm (about 20 psi). About 70 μg of the wet coating was applied. The wet coating was baked at about 140° C. for about 2 hours, yielding a dry primer layer.

A second composition was prepared by mixing the following components:
  (a) about 2.0 mass % of EVAL;
  (b) about 1.6 mass % of EVEROLIMUS; and
  (c) the balance, DMAC solvent.

The second composition was applied onto the dried primer layer to form a drug-polymer layer, using the same spraying technique and equipment used for applying the primer layer. About 300 μg of the wet coating was applied, followed by drying, e.g., by baking as described above. The dry drug-polymer layer contained about 130 μg of EVEROLIMUS.

A third composition was prepared by mixing the following components:
  (a) about 2 mass % of PBMA having $M_n$ of about 154,000; and
  (b) about 0.1 mass % of PEG having $M_n$ of about 18,000; and
  (c) the balance, a 1:1 by mass mixture of solvents, acetone and cyclohexanone.

The third composition was applied onto the dried drug-polymer layer, to form a topcoat layer, using the same spraying technique and equipment used for applying the primer and the drug-polymer layers. About 200 μg of the wet coating was applied, followed by drying, e.g., by baking as described above. The final amount of the dried topcoat was about 50 μg.

The kinetics of release of EVEROLIMUS in vitro was studied chromatographically (HPLC). To study the kinetics, three stents were coated as described above in this Example. The amount of EVEROLIMUS released from a stent coating having the PBMA-PEG topcoat was measured. The average of the data obtained from the three stents was used to plot a curve 1. As a control, two identical control stents were used, except the topcoat included only pure PBMA instead of PBMA-PEG. A control curve 2 was plotted using the average of the data obtained from the two control stents. The rate of release of EVEROLIMUS through the PBMA-PEG topcoat is about twice the rate of release through the PBMA topcoat.

EXAMPLE 5

A primer and drug-polymer layers can be formed on a stent as described in Example 4, but instead of EVEROLIMUS, rapamycin can be used. A topcoat composition can then be prepared by mixing the following components:
  (a) about 2 mass % of PBMA having $M_n$ of about 154,000; and
  (b) about 0.05 mass % of PEG having $M_n$ of about 18,000;
  (c) about 0.05 mass % of poly(propylene glycol) (PPG) having $M_n$ of about 40,000; and
  (c) the balance, a 1:1 by mass mixture of solvents, acetone and cyclohexanone.

If desired, poly(tetramethylene glycol) (PTMG) can be used in the topcoat composition instead of PPG. The $M_n$ of PTMG can also be about 40,000. A PPG/PTMG blend having any ratio between PPG and PTMG can also be optionally used instead of PPG. In this example, in the topcoat composition the mass ratio between PEG and PPG is 1:1. If desired, the amount of PPG or PTMG, or a mixture thereof can be up to about twice amount of PEG. Optionally, all of the PEG in the topcoat composition can be replaced with PPG or PTMG, or with a mixture thereof.

The topcoat composition can be applied onto the dried drug-polymer layer, to form a topcoat layer, using the same spraying technique and equipment used for applying the primer and the drug-polymer layers. About 200 μg of the wet coating can be applied, followed by drying, e.g., by baking as described above. The final amount of the dried topcoat can be about 50 μg.

EXAMPLE 6

A primer and drug-polymer layers can be formed on a stent as described in Example 4. A topcoat composition can then be prepared by mixing the following components
  (a) between about 1.0 mass % and about 15 mass %, for example, about 1.9 mass % of poly(hexafluoropropene-co-vinylidene fluoride) (PHFP-VDF) having $M_n$ about 125,000.

(b) between about 0.04 mass % and about 0.8 mass %, for example, about 0.1 mass % of F127 PLURONIC copolymer; and
(c) the balance, a mixture of solvents, the solvent mixture including acetone and cyclohexanone in a mass ratio of about 1:1.

F127 PLURONIC is a difunctional poly(ethylene oxide)-poly(propylene oxide)-poly(ethylene oxide) triblock copolymer terminating in primary hydroxyl groups. F127 PLURONIC has $M_n$ of about 12,600.

The topcoat composition can be applied onto the dried drug-polymer layer, to form a topcoat layer, using the same spraying technique and equipment used for applying the primer and the drug-polymer layers. About 200 µg of the wet coating can be applied, followed by drying, e.g., by baking as described above. The final amount of the dried topcoat can be about 50 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate and a coating, the coating comprising:
   a bulk polymer selected from a group consisting of a poly(meth)acrylate, a vinyl polymer, a halogenated polymer, and a polymer having urethane groups;
   an additive polymer in less quantity in the coating than the bulk polymer, the additive polymer being entangled with the bulk polymer; and
   a drug;
   wherein the bulk polymer has an equilibrium water adsorption less than about 10 mass % at room temperature;
   wherein the poly(meth)acrylate is poly(n-propyl methacrylate), poly(iso-propyl methacrylate), poly(n-propyl acrylate), poly(iso-propyl acrylate), poly(n-butyl acrylate), poly(iso-butyl acrylate), or a mixture thereof;
   wherein the vinyl polymer is poly(ethylene-co-vinyl acetate), poly(styrene-co-iso-butylene), poly(styrene-co-ethylene-co-butylene-co-styrene) terpolymer, poly(styrene-co-butadiene-co-styrene) terpolymer, or a mixture thereof;
   wherein the halogenated polymer is poly(vinyl fluoride), poly(vinylidene fluoride), polyhexafluoropropene, poly(hexafluoropropene-co-vinylidene fluoride), poly(ethylene-co-hexafluoropropene), poly(vinyl chloride), poly(vinylidene chloride), or a mixture thereof;
   wherein the polymer having urethane groups is a polyurethaneurea, a silicone urethane, or a mixture thereof;
   wherein the additive polymer is chondroitan sulfate, a glucosaminoglucan, dextrin, dextran sulfate, or a mixture thereof, or poly(trimethylene glycol), poly(tetramethylene glycol), or a mixture thereof; and
   wherein the ratio of the bulk polymer to the additive polymer is about 74:1 to about 14:1.

2. The medical article of claim 1, wherein the ratio of the bulk polymer to the additive polymer is about 49:1 to about 19:1.

3. The medical article of claim 1, wherein the bulk polymer is more hydrophobic than the additive polymer.

4. The medical article of claim 1, wherein the bulk polymer is a poly(meth)acrylate selected from the group consisting of poly(n-propyl methacrylate), poly(iso-propyl methacrylate), poly(n-propyl acrylate), poly(iso-propyl acrylate), poly(n-butyl acrylate), poly(iso-butyl acrylate), and mixtures thereof.

5. The medical article of claim 1, wherein the additive polymer is selected from the group consisting of poly(trimethylene glycol), poly(tetramethylene glycol), and mixtures thereof.

6. The medical article of claim 1, wherein the bulk polymer has a Hildebrand solubility parameter lower than 10.7 (cal/cm$^3$)$^{1/2}$.

7. The medical article of claim 1, wherein the bulk polymer is a vinyl polymer.

8. The medical article of claim 1, wherein the bulk polymer is a halogenated polymer.

9. The medical article of claim 1, wherein the bulk polymer is a polymer having urethane groups.

10. The medical article of claim 1, wherein the article is a stent.

11. The medical article of claim 1, wherein the drug is selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, and combinations thereof.

12. The medical article of claim 1, wherein the vinyl polymer is poly(styrene-co-iso-butylene), poly(styrene-co-ethylene-co-butylene-co-styrene) terpolymer, poly(styrene-co-butadiene-co-styrene) terpolymer, or a mixture thereof.

13. The medical article of claim 1, wherein the halogenated polymer is poly(vinyl fluoride), poly(vinylidene fluoride), poly(vinyl chloride), poly(vinylidene chloride), or a mixture thereof.

14. The medical article of claim 1, wherein the halogenated polymer is polyhexafluoropropene, poly(hexafluoropropene-co-vinylidene fluoride), poly(ethylene-co-hexafluoropropene), poly(vinyl chloride), poly(vinylidene chloride), or a mixture thereof.

15. The medical article of claim 1, wherein the additive polymer is chondroitan sulfate, a glucosaminoglucan, dextrin, dextran sulfate, or a mixture thereof.

16. A medical article comprising an implantable substrate and a coating, the coating comprising:
   a bulk polymer selected from a group consisting of poly(styrene-co-iso-butylene), poly(styrene-co-ethylene-co-butylene-co-styrene) terpolymer, poly(styrene-co-butadiene-co-styrene) terpolymer, and a mixture thereof;
   an additive polymer in less quantity in the coating than the bulk polymer, the additive polymer being entangled with the bulk polymer; and
   a drug;
   wherein the bulk polymer has an equilibrium water adsorption less than about 10 mass % at room temperature;
   wherein the additive polymer is chondroitan sulfate, a glucosaminoglucan, dextrin, dextran sulfate, carboxymethyl cellulose, a cellulosic, poly(ethylene amine), poly(allyl amine), a non-ionic tetrafunctional block-copolymer surfactant, gelatin, collagen, albumin, chitin, elastin, fibrin, or a mixture thereof, or poly(trimethylene glycol), poly(tetramethylene glycol), or a mixture thereof; and
   wherein the ratio of the bulk polymer to the additive polymer is about 74:1 to about 14:1.

17. The medical article of claim 16, wherein the ratio of the bulk polymer to the additive polymer is about 49:1 to about 19:1.

18. The medical article of claim 16, wherein the bulk polymer is more hydrophobic than the additive polymer.

19. The medical article of claim 16, wherein the additive polymer is selected from the group consisting of poly(trimethylene glycol), poly(tetramethylene glycol), and mixtures thereof.

20. The medical article of claim 16, wherein the bulk polymer has a Hildebrand solubility parameter lower than 10.7 $(cal/cm^3)^{1/2}$.

21. The medical article of claim 16, wherein the article is a stent.

22. The medical article of claim 16, wherein the drug is selected from the group consisting of rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, and combinations thereof.

23. The medical article of claim 16, wherein the additive polymer is chondroitan sulfate, a glucosaminoglucan, dextrin, dextran sulfate, or a mixture thereof, or poly(trimethylene glycol), poly(tetramethylene glycol), or a mixture thereof.

* * * * *

UNITED STATES PATENT AND TRADEMARK OFFICE
CERTIFICATE OF CORRECTION

PATENT NO. : 8,673,334 B2  
APPLICATION NO. : 11/903176  
DATED : March 18, 2014  
INVENTOR(S) : Pacetti et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this
Eleventh Day of August, 2015

Michelle K. Lee
*Director of the United States Patent and Trademark Office*